US00RE39530E

(19) United States
(12) Reissued Patent
Sundermann et al.

(10) Patent Number: US RE39,530 E
(45) Date of Reissued Patent: Mar. 27, 2007

(54) 3-AMINO-3-ARYLPROPAN-1-OL-COMPOUNDS, THEIR PREPARATION AND USE

(75) Inventors: Bernd Sundermann, Aachen (DE); Hagen-Heinrich Hennies, Simmerath (DE); Babette-Yvonne Koegel, Langerwehe-Hamich (DE); Helmut Buschmann, Esplugues de Llobregat (ES)

(73) Assignee: Gruenenthal GmbH, Aachen (DE)

(21) Appl. No.: 10/659,680

(22) Filed: Sep. 11, 2003

Related U.S. Patent Documents

Reissue of:
(64) Patent No.: 6,288,278
Issued: Sep. 11, 2001
Appl. No.: 09/545,519
Filed: Apr. 7, 2000

(30) Foreign Application Priority Data

Apr. 7, 1999 (DE) ..... 199 15 602

(51) Int. Cl.
*A61K 31/135* (2006.01)

(52) U.S. Cl. ..... 514/655; 514/445; 514/473; 564/391; 564/384; 564/389; 564/336; 560/73; 549/65; 549/479

(58) Field of Classification Search ..... 564/391, 564/384, 389, 336; 560/73; 549/65, 479; 514/534, 655, 473, 445
See application file for complete search history.

(56) References Cited

U.S. PATENT DOCUMENTS 3,937,818 A 2/1976 Fletcher et al.
3,975,436 A 8/1976 Fletcher et al.
4,017,637 A * 4/1977 Yardley et al. ..... 424/311
4,143,158 A 3/1979 Lien et al.

FOREIGN PATENT DOCUMENTS

EP 1043307 A2 10/2000

OTHER PUBLICATIONS

European Search Report.
Carlson et al., "Improved Titanium Tetrachloride Procedure for Enamine Sunthesis. II. Scope of the Reaction", *Acta Chemica Scandinavica B 38,* 1984, pp. 49–53.*
Risch et al., "Additions of Enamines to Iminium Ions", *Houben–Weyl* E21b, 1995, pp. 1925–1929.*
Risch et al., "Diastereomerenreine Mannich–Based durch Addition von Enaminen an ternäre Iminiumsalze", *Agnew. Chem,* 106, 1994, pp. 2531–2533.*
Arend et al., "A Simple and Highly Diastereoselective One–Pot Synthesis of Mannich–Bases", *Synlett,* Jun. 17, 1997, pp. 974–976.*
Winterfeldt, "Applications of Diisobutylaluminium Hydride (DIBAH) and Triisobutylaluminium (TIBA) as Reducing Agents in Organic Synthesis", *Synthesis,* Oct. 1975, pp. 617–630.*
Hendershot et al., "Antagonism of the Frequency of Phenylquinone–Induced Writhing in the Mouse by Weak Analgesics and Nonanalgesics", *J. Pharmacol. Exp. Ther.,* 1959, pp. 237–240.*
Schoemaker et al., "[$^3$H]Diltiazem Binding to Calcium Channel Antagonists Recognition Sites in Rat Cerebral Cortex", *European Journal of Pharmacology* 111, 1985, pp. 273–277.*
Gray et al., "The Isolation of Nerve Endings from Brain: an Electron–Microscopic Study of Cell Fragments Derived by Homogenization and Centrifugation", *J. Anat.* 96, 1962, pp. 79–88.*
Pauwels et al., "[$^3$H]Batrachotoxinin A 20–α–Benzoate Binding to Sodium Channels in Rat Brain: Characterization and Pharmacological Significance", *European Journal of Pharmacology* 124, 1986, pp. 291–298.*
Cheng et al., "Relationship Between the Inhibition Constant ($K_I$) and the Concentration of Inhibitor Which Causes 50 per cent Inhibition ($I_{50}$) of an Enzymatic Reaction", *Biochem. Pharmacology,* vol. 22, 1973, pp. 3099–3108.*
Lineweaver et al., "The Determination of Enzyme Dissociation Constants", *J. Am. Chem. Soc.,* vol. 56, 1934, pp. 658–666.*
Lieberman, "The Use of the Disproportion of Esters of 2–Propanenitronic Acid to Convert Halides to Carbonyl Compounds and Benzaldehyde to Benzamides", *J. Am. Chem. Soc.* 77, 1955, pp. 1114–1116.*
Goodman & Gilman, "The Pharmacological Basis of Therapeutics", 9$^{th}$ Edition, Section III, Chapter 23, (1991).*
Larock, "Comprehensive Organic Transformations", VCH Publishers, (1989), pp. 966–973.*

* cited by examiner

*Primary Examiner*—Samuel Barts
(74) *Attorney, Agent, or Firm*—Crowell & Moring LLP

(57) ABSTRACT

3-amino-3-arylpropan-1-ol compounds corresponding to the formula I

I

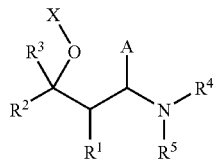

in which $R^1$ to $R^5$, A and X have the meanings according to claim 1, and their preparation and use as medicaments.

32 Claims, No Drawings

3-AMINO-3-ARYLPROPAN-1-OL-COMPOUNDS, THEIR PREPARATION AND USE

Matter enclosed in heavy brackets [ ] appears in the original patent but forms no part of this reissue specification; matter printed in italics indicates the additions made by reissue.

FIELD OF THE INVENTION

The invention relates to 3-amino-3-arylpropan-1-ol derivatives corresponding to the formula formula I

I

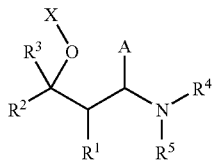

wherein $R^1$, $R^2$ each independently of one another denote $C_{1-6}$-alkyl, or $R^1$ and $R^2$ together form a $(CH_2)_{2-6}$ ring, which can also be benzo-fused or phenyl-substituted, $R^3$ denotes H or methyl, $R^4$, $R^5$ each independently of one another denote $C_{1-6}$-alkyl, $C_{3-6}$-cycloalkyl, phenyl, benzyl or phenethyl, or $R^4$ and $R^5$ together form a $(CH_2)_{3-6}$ or $CH_2CH_2OCH_2CH_2$ ring, A denotes an aryl radical, which optionally may contain heteroatoms in the ring system and/or may be substituted, X denotes a substituted benzyl of the formula XI

XI

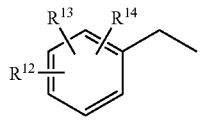

or a substituted benzoyl of the formula XII

XII

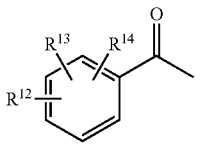

wherein $R^{12}$ to $R^{14}$ in each independently of one another denote H, F, Cl, Br, $CHF_2$, $CF_3$, $OR^{11}$, $SR^{11}$, $OCF_3$, $SO_2CH_3$, $SO_2CF_3$, $C_{1-6}$-alkyl, phenyl, CN, $COOR^{11}$ or $NO_2$, where $R^{11}$ denotes H, $C_{1-6}$-alkyl, phenyl, benzyl or phenethyl, and diastereomers or enantiomers thereof, in the form of their bases or salts of physiologically tolerated acids, and their preparation and use as medicaments.

BACKGROUND OF THE INVENTION

The treatment of chronic and non-chronic states of pain is of great importance in medicine since pain is clinically one of the basic symptoms. There is currently a worldwide demand for additional pain treatment which is not exclusively opioid but has a good efficacy. The urgent need for action in respect of patient-relevant and target-oriented treatment of chronic and non-chronic states of pain, this being understood as meaning successful and satisfactory pain treatment for the patient, is documented in the large number of scientific works which have recently appeared in the field of applied analgesia and fundamental research into nociception.

Conventional opioids, such as e.g. morphine, have a good action in the treatment of severe to very severe pain. However, their use is limited due to the known side effects, e.g. respiratory depression, vomiting, sedation, constipation, addiction, dependency and development of tolerance. They can therefore be administered over a relatively long period of time or in relatively high dosages only with particular safety precautions, such as e.g. specific prescription instructions (Goodman, Gilman, The Pharmacological Basis of Therapeutics, Pergamon Press, New York 1990). Furthermore, they are not very effective for some states of pain, in particular neuropathic pain.

SUMMARY OF THE INVENTION

The object of the invention was to provide a new structural class of analgesically active substances which are suitable for treatment of pain.

A further object was to discover active compounds which are also suitable for use as a local anaesthetic and/or antiarrhythmic and/or antiemetic and/or nootropic (neurotropic) and/or for treatment or therapy of cardiovascular diseases and/or urinary incontinence and/or diarrhea and/or pruritus and/or alcohol, drug or medicament dependency and/or inflammations.

It has been found that the class of compounds corresponding to formula I is distinguished by a pronounced analgesic action. The compounds of the general formula I furthermore show a clear affinity for bonding site 2 of the sodium channel (BTX bonding) and for the benzothiazepine bonding site of the L-type calcium channel (diltiazem bonding). As a result, the class of compounds of formula I is also suitable for use as (i.e., for the preparation of a medicament for) a local anaesthetic and/or antiarrhythmic and/or antiemetic and/or nootropic (neurotropic) and/or for treatment/therapy of cardiovascular diseases and/or urinary incontinence and/or diarrhea and/or pruritus and/or alcohol and/or drug or medicament dependency and/or inflammations.

The invention therefore relates to 3-amino-3-arylpropan-1-ol derivatives corresponding to the formula I and diastereomers or enantiomers thereof, in the form of their bases or salts of physiologically acceptable adds.

Preferred compounds are:

compounds of formula I in which $R^1$ and $R^2$ together form a $(CH_2)_{2-6}$-ring, which can also be benzo-fused or phenyl-substituted, and $R^3$ to $R^5$, A and X have the meanings according to the definition of the general formula I, or compounds of formula I in which $R^1$ and $R^2$ together form a $(CH_2)_4$ ring, which may also be benzo-fused or phenyl-substituted, and $R^3$ to $R^5$, A and X have the meanings according to the definition of the general formula I, or compounds of formula I in which $R^3$ represents hydrogen and $R^1$, $R^2$, $R^4$, $R^5$, A and X have the meanings according to the definition of the general formula I, or compounds of formula I in which A denotes a substituted phenyl of formula XIII

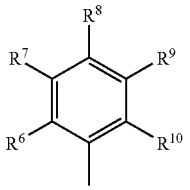

wherein $R^6$ to $R^{10}$ each independently of one another denote H, F, Cl, Br, I, $CF_3$, OH, $OR^{11}$, $OCF_3$, $SR^{11}$, $SO_2CH_3$, $SO_2CF_3$, $C_{1-6}$-alkyl, phenyl, CN, $COOR^{11}$ or $NO_2$, or $R^6$ and $R^7$ or $R^7$ and $R^8$ together form an $OCH_2O$ or $OCH_2CH_2O$ ring, and $R^{11}$ denotes $C_{1-6}$-alkyl, phenyl, benzyl or phenethyl, or a substituted or unsubstituted thiophene radical or furan radical, and $R^1$ to $R^5$ and X have the meanings according to the definition of the general formula I, or compounds of formula I in which $R^1$ and $R^2$ together form a $(CH_2)_{2-6}$ ring, which can also be benzo-fused or phenyl-substituted, $R^3$ represents hydrogen, and $R^4$, $R^5$, A and X have the meanings according to the definition of the general formula I, or compounds of formula I in which $R^1$ and $R^2$ together form a $(CH_2)_4$ ring, which can also be benzo-fused or phenyl-substituted, A represents a substituted phenyl group of formula XIII or a substituted or unsubstituted thiophene radical or furan radical, $R^3$ represents hydrogen, and $R^4$, $R^5$ and X have the meanings according to the definition of the general formula I, or compounds of formula I in which $R^1$ and $R^2$ together form a $(CH_2)_4$ ring, A represents a substituted phenyl group of formula XIII or a substituted or unsubstituted thiophene radical or furan radical, $R^3$ represents hydrogen, and $R^4$, $R^5$ and X have the meanings according to the definition of the general formula I, or compounds of formula I in which $R^1$ and $R^2$ together form a $(CH_2)_4$ ring, A represents a substituted or unsubstituted thiophene radical, $R^3$ represents hydrogen, and $R^4$, $R^5$ and X have the meanings according to the definition of the general formula I, or compounds of formula I in which $R^1$ and $R^2$ together form a $(CH_2)_4$ ring, A represents a substituted or unsubstituted furan radical, $R^3$ represents hydrogen, and $R^4$, $R^5$ and X have the meanings according to the definition of the general formula I, or compounds of formula I in which X represents a substituted benzyl radical of formula XI, and $R^1$ to $R^5$ and A have the meanings according to the definition of general formula I.

Further preferred compounds include:

dimethyl-{[2-(2-methylbenzyloxy)cyclohexyl]phenylmethyl}-amine and the corresponding hydrochloride;

[2-(dimethylaminophenylmethyl)cyclohexyl]4-trifluoromethylbenzoate and the corresponding hydrochloride;

[2-(dimethylaminophenylmethyl)cyclohexyl]4-methoxybenzoate and the corresponding hydrochloride;

{[2-(2-chlorobenzyloxy)cyclohexyl]-(2-chlorophenyl)methyl}-dimethylamine and the corresponding hydrochloride;

{(2-chlorophenyl)-[2-(4-methylbenzyloxy)cyclohexyl]methyl}-dimethylamine and the corresponding hydrochloride;

{[2-(4-fluorobenzyloxy)cyclohexyl]phenylmethyl}-dimethylamine and the corresponding hydrochloride.

In a particular embodiment of the invention, the enantiomers of a compound according to the invention are employed in a non-equimolar ratio, the content of one enantiomer in the enantiomer mixture preferably being 5 to 45 per cent by weight, as an active compound in a medicament, which can optionally comprise further active compounds.

In the context of the present invention, the term "$C_{1-6}$-alkyl", denotes straight-chain or branched hydrocarbons having 1 to 6 carbon atoms. Examples include methyl, ethyl, propyl, isopropyl, n-butyl, sec-butyl, tert-butyl, n-pentyl, neopentyl and n-hexyl.

In the context of the present invention, the term "$C_{3-7}$-cycloalkyl" denotes saturated cyclic hydrocarbons or straight-chain or branched alkyl radicals which contain saturated cyclic hydrocarbons, having a total of 3 to 7 carbon atoms. Examples include cyclopropyl, cyclopropylmethyl, methylcyclopropyl, cyclobutyl, 1-cyclopropylethyl, 2-cyclopropylethyl, cyclopentyl, cyclopentylmethyl, cyclohexyl or cycloheptyl.

In the context of the present invention, the term "aryl" denotes preferably aromatic carboxylic radicals which are unsubstituted or optionally mono- or polysubstituted by the radicals $R^6$ to $R^{10}$ according to formula XIII and may contain heteroatoms in the ring system. Aryl is preferably a substituted phenyl group of formula XIII.

In the context of the present invention, aryl radicals with heteroatoms preferably denote 5- or 6-membered unsaturated heterocyclic compounds which contain one or two heteroatoms, such as nitrogen, oxygen and/or sulfur, are optionally fused with further rings, and are unsubstituted or mono- or polysubstituted with the radicals $R^6$ to $R^{10}$ according to formula XIII. Examples of unsaturated heterocyclic compounds include furan, thiophene, pyrrole, pyridine, pyrimidine, quinoline, isoquinoline, phthalazine or quinazoline.

The present invention also provides processes for the preparation of compounds of general formula I. To prepare the compounds of formula I, the Mannich bases of formula II are reacted with a suitable nucleophile, such as, for example, an organometallic compound $(H_3C)Y$, in which Y denotes, for example, MgCl, MgBr, MgI or Li, or a reducing agent, such as, for example, sodium borohydride, sodium cyanoborohydride, lithium aluminium hydride, diisobutylaluminium hydride or a complex analogue of these compounds, at temperatures of between −70° C. and +110° C. Ethers or esters of the general formula I can be obtained from the corresponding alcohols by standard methods by reacting the alcohols with corresponding benzyl or benzoyl halides in the presence of inorganic or organic bases. Esters can also be obtained by condensing the alcohols with carboxylic acids (R. C. Larock; Comprehensive Organic Transformations; VCH Publishers; New York, Weinheim, Cambridge 1989).

II

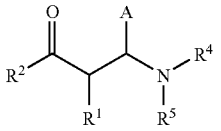

The reaction of a Mannich base of the formula II with a Grignard compound MeY, in which Y denotes MgCl, MgBr or MgI, or with an organolithium compound MeLi can be carried out in an aliphatic ether, for example diethyl ether and/or tetrahydrofuran, a hydrocarbon, for example hexane or toluene, or mixtures of hydrocarbons and aliphatic ethers at temperatures between −70° C. and +110° C. Organolithium compounds MeLi can be obtained from organohalogen compounds MeZ, in which Z denotes Cl, Br or I, by halogen-lithium exchange by reaction with, for example, an n-butyllithium/hexane solution.

In the reaction of a Mannich base of the formula II with an organometallic compound MeY, tertiary alcohols with the relative configuration of the formula Ia, in which the aminoarylmethyl group is in the cis position relative to the hydroxyl group, if $R^1$ and $R^2$ form a ring system, are preferentially obtained, depending on the reaction conditions. In the case of open-chain systems, the analogous relative stereochemistry is obtained, this being specified as anti. The compounds of the formula Ia can be obtained in a diastereomerically pure form by separation by column chromatography or by crystallization, also of their salts, for example the hydrochlorides.

Ia

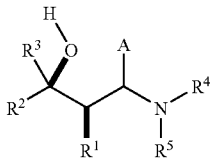

The reaction of a Mannich base of the formula II with a reducing agent can be carried out in alcohols, water, an ether, a hydrocarbon, a halogenohydrocarbon or mixtures of these solvents at temperatures of between −70° C. and +110° C.

The reaction conditions can be chosen here such that one of the two possible stereoisomers Ib and Ic is obtained preferentially or exclusively.

Ib

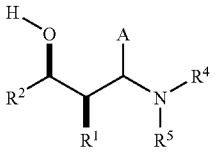

Ic

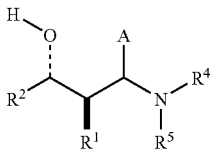

The Mannich bases of the formula II can be obtained by reaction of enamines of the formula III with an imminium salt of formula IV, in which Y denotes, for example, $Cl^-$, $AlCl_4^-$, $Br^-$ or $I^-$.

III

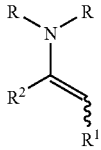

IV

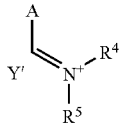

The enamines are prepared by processes known from the literature from ketones of formula V and secondary amines, for example dimethylamine, pyrrolidine, piperidine or morpholine (Acta Chem. Scand. B 38 (1984) 49–53). The imminium salts are prepared by processes known from the literature by reaction of aminals of formula VI with acid chlorides, for example acetyl chloride or thionyl chloride (Houben-Weyl—Methoden der Organischen Chemie [Methods of Organic Chemistry], E21b (1995)1925–1929).

V

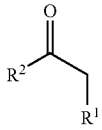

VI

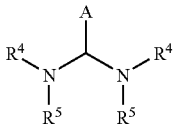

VII

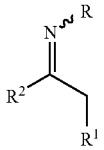

The imminium salts of formula IV do not have to be isolated here, but can be produced in situ and reacted with enamines of formula III to give Mannich bases of formula II (Angew. Chem. 106 (1994) 2531–2533). Based on the enamine-imine tautomerism analogous to keto-enol tautomerism, imines of formula VII can also be employed instead of the enamines of formula III. Alternatively, ketones of formula V can also be reacted directly with imminium salts of formula IV.

However, Mannich bases of formula II can also be prepared directly by reaction of enamines of formula III with an aromatic aldehyde of formula VIII and a secondary amine $HNR^4R^5$, also in the form of the corresponding hydrochloride $HNR^4R^5$, HCl, in the presence of triethylamine, chlorotrimethylsilane and sodium iodide (Synlett (1997) 974–976).

VIII

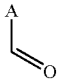

The Mannich bases of formula II are preferably obtained by the processes described above with the relative configuration of formula IIa, in which the amino group is in the anti position relative to $R^1$, depending on the reaction conditions. The compounds of formula IIa can be obtained in a diastereomerically pure form by crystallization, also of their salts, for example hydrochlorides, or by chromatographic separation.

IIa

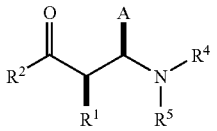

On the other hand, the preparation of Mannich bases of formula II proceeds less stereoselectively by 1,4-addition of secondary amines $HNR^4R^5$ on to enones of formula IX, which are obtained by aldol condensation of ketones of formula V with aromatic aldehydes of formula VIII (U.S. Pat. No. 4,017,637). This procedure is therefore suitable for the preparation of the other possible stereoisomers.

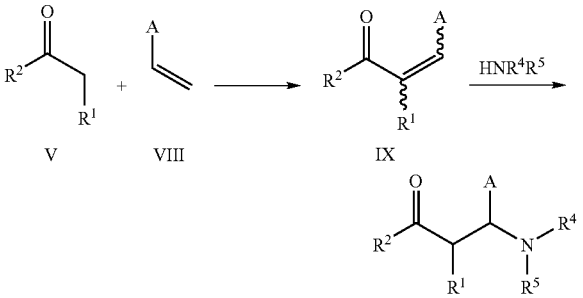

V VIII IX

II

The meanings of the radicals $R^1$ to $R^5$ and A correspond to the meanings according to formula I.

If chiral amines are employed for the preparation of enamines of formula III or imines of formula VII, enantiomerically concentrated to enantiomerically pure Mannich bases of formula II can be obtained in the subsequent Mannich reaction (Houben-Weyl—Methoden der Organischen Chemie [Methods of Organic Chemistry], E21b (1995) 1925–1929).

3-Amino-3-arylpropan-1-ol derivatives of formula I which are substituted by a phenol can be prepared, for example, from the corresponding methyl ether derivatives with diisobutylaluminium hydride in an aromatic hydrocarbon, for example toluene, at a temperature of between 60 and 130° C. (Synthesis (1975) 617–630).

The compounds of formula I can be converted into their salts in a known manner with physiologically acceptable acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, for example diethyl ether, diisopropyl ether, acetic acid alkyl esters, acetone and/or 2-butanone. Trimethylchlorosilane in aqueous solution is moreover suitable for the preparation of the hydrochlorides.

The substances corresponding to formula I are toxicologically acceptable, so that they are suitable for use as a pharmaceutical active compound in medicaments. The present invention therefore also provides medicaments comprising at least one compound of formula I as an active compound. The medicaments according to the invention are preferably suitable as analgesics.

Biochemical investigations have shown that the substances according to the invention also show, in addition to their analgesic action, a pronounced affinity for bonding site 2 of the sodium channel (BTX bonding) and for the benzothiazepine bonding site of the L-type calcium channel (diltiazem bonding). Thus, in addition to the particularly preferred use in the treatment of pain, the substances according to the invention are also suitable for use as a local anaesthetic and/or antiarrhythmic and/or antiemetic and/or nootropic (neurotropic) and/or for treatment or therapy of cardiovascular diseases and/or urinary incontinence and/or diarrhea and/or pruritus and/or alcohol, drug or medicament dependency and/or inflammations.

The pharmaceutical formulations comprise, in addition to at least one 3-amino-3-arylpropan-1-ol derivative of formula I, carrier materials, fillers, solvents, diluents, dyestuffs and/or binders. The choice of auxiliary substances and the amounts thereof to be employed depend on whether the medicament is to be administered orally, intravenously, intraperitoneally, intradermally, intramuscularly, intranasally, buccally or locally, for example on infections on the skin, the mucous membranes and on the eyes. Formulations in the form of tablets, coated tablets, capsules, granules, drops, juices and syrups are suitable for oral administration, and solutions, suspensions, dry formulations which can easily be reconstituted and sprays are suitable for parenteral, topical and inhalatory administration. Compounds of formula I according to the invention in a depot, in dissolved form or in a patch, optionally with the addition of agents which promote penetration through the skin, are suitable formulations for percutaneous administration. Formulation forms which can be used orally or percutaneously can release the compounds of formula I according to the invention in a delayed-release manner.

The amount of active compound to be administered to the patients varies according to the weight of the patient, the mode of administration, the indication and the severity of the illness. 0.5 to 500 mg/kg of at least one 3-amino-3-arylpropan-1-ol derivative of the formula I are usually administered.

PHARMACOLOGICAL STUDIES

Testing of the Analgesia in the Writhing Test on Mice

The analgesic activity was investigated on phenylquinone-induced writhing in mice (modified by I. C. Hendershot and J. Forsaith (1959) J. Pharmacol. Exp. Ther. 125, 237–240). Male NMRI mice weighing 25 to 30 g were used for this. Groups of 10 animals per dose of substance received 0.3 ml/mouse of a 0.02% aqueous solution of phenylquinone (phenylbenzoquinone), Sigma, Deisenhofen; preparation of the solution with addition of 5% ethanol and storage in a water bath at 45° C.) as an intraperitoneal administration 10 minutes after intravenous administration of the test substances. The animals were placed individually in observation cages. The number of pain-induced extension movements (so-called writhing reactions=straightening of the body with stretching out of the hind extremities) 5 to 20 minutes after the administration of phenylquinone was counted by means of a push-button counter. Animals which receive only physiological saline solution were also run as a control. All the substances were tested in the standard dosage of 10 mg/kg. The percentage inhibition (% inhibition) of the writhing reaction by a substance was calculated in accordance with the following equation:

$$\% \text{ inhibition} = 100 - \frac{\text{Writhing reactions of the treated animals}}{\text{Writhing reactions of the control animals}} * 100$$

For some substances, the $ED_{50}$ values with 95% confidence limits of the writhing reaction were calculated from the dose-dependent decrease in the writhing reactions compared with phenylquinone control groups investigated in parallel by means of regression analysis (evaluation program of Martens EDV Service, Eckental).

All the compounds according to the invention investigated showed a pronounced analgesic action. The results are summarized in table 1.

TABLE 1

| Testing of the analgesia in the writhing test on mice | |
|---|---|
| Example | % Inhibition of the writhing reaction at 10 mg/kg intravenously |
| 1 | 85 |
| 2 | 48 |
| 3 | 43 |
| 4 | 32 |
| 5 | 74 |
| 6 | 68 |

BIOCHEMICAL STUDIES

Bonding Investigations on the L Calcium Channel Benzothiazepine Bonding Site (diltiazem bonding)

The biological membrane material was isolated from the cerebrocortex of the rat. [$^3$H]-cis-(+)-Diltiazem (5 nM in the batch) was used as the ligand. Incubation for 20 minutes at 25° C. The radioactivity measured in the presence of (+)-diltiazem ($10^{-6}$ M in the batch) is defined as non-specific bonding. At the end of the incubation, the non-bonded content of radioactive ligand is removed with the aid of a filtration process over Whatman glass fiber GF/B membranes. After a washing process, the membranes are then measured on a β-counter. The method has been established in accordance with the publication of Schoemaker and Langer (H. Schoemaker and S. Z. Langer (1985) Eur. J. Pharmacol. 111, 273–277). The $K_D$ value for this high-affinity bonding site was determined as 4.10±0.75 nM (N=3, i.e. means±SEM from 3 independent test series which have been carried out in triplicate parallel experiments).

Bonding Investigations on the Sodium Channel Bonding Site 2 (BTX bonding)

Bonding site 2 of the sodium channel is the so-called batrachotoxin (BTX) bonding site. [$^3$H]-Batrachotoxin A20 α-benzoate (10 nM in the batch) was employed as the ligand. These ion channel particles (synaptosomes) were concentrated out of the rat cerebrocortex by the method of Gray and Whittaker (E. G. Gray and V. P. Whittaker (1962) J. Anat. 76, 79–88). The radioactivity measured in the presence of veratridin (0.3 mM in the batch) is defined as non-specific bonding. Incubation at 37° C. for 120 min. The assay conditions were implemented in accordance with the publication of Pauwels, Leysen and Laduron (P. J. Pauwels, J. E. Leysen and P. M. Laduron (1986) Eur. J. Pharmacol. 124, 291–298).

The $K_D$ value for this bonding site is at 24.63±1.56 nM (N=3, i.e. means±SEM from 3 independent test series which have been carried out in triplicate parallel experiments).

Evaluation

In addition to the percentage inhibition of the test systems at fixed test substance concentrations (10 μM in the batch), dose-dependencies were investigated. In this investigation, $IC_{50}$ values are obtained, and these can be converted by the "Cheng-Prusoff equation" (Y. C. Cheng and W. H. Prusoff (1973) Biochem. Pharmacol. 22, 3099–3108) into inhibitor constants ($K_i$). The $IC_{50}$ values were obtained with the aid of the "Figure P" computer program (version 6.0, Biosoft, Cambridge, England). Km values were calculated by the method of Lineweaver and Burk (H. Lineweaver and D. Burk (1934) J. Am. Chem. Soc. 56, 658–666). The "Ligand" computer program (version 4, Biosoft, England) is used to obtain $K_D$ values.

The results of the biochemical studies are shown in table 2.

TABLE 2

| Biochemistry | | |
|---|---|---|
| Example | Diltiazem bonding at 10 μM | BTX bonding at 10 μM |
| 1 | 82 | 99 |
| 2 | | 98 |
| 3 | 65 | 89 |
| 4 | 73 | 92 |
| 5 | 89 | 98 |
| 6 | 86 | 97 |

EXAMPLES

The following examples serve to illustrate the process according to the invention in more detail without restricting the scope of the invention. The yields of the compounds prepared are not optimized. All the temperatures are uncorrected. The term ether refers to diethyl ether. Silica gel 60 (0.040–0.063 mm) from E. Merck, Darmstadt was employed as the stationary phase for the column chromatography. The thin layer chromatography studies were carried out using HPTLC pre-coated plates, silica gel 60 F 254 from E. Merck, Darmstadt. Separations of racemates were carried out on a Chiracel OD column 250×4.6 mm with a pre-column from Daicel. The mixing ratios of the mobile phase for all the chromatographic investigations are always stated in volume/volume. RT denotes room temperature; vol. % denotes per cent by volume; wt. % denotes per cent by weight, and % ee denotes enantiomer excess in per cent.

Example 1

Dimethyl-{[2-(2-methyl-benzyloxy)cyclohexyl] phenylmethyl}-amine hydrochloride.

1st stage:

Benzylidenedimethylammonium chloride.

10 g (56 mmole) of N,N,N', N'-tetramethyl-C-phenylmethanediamine (J. Am. Chem. Soc. 77 (1955) 1114–1116) were dissolved in 100 ml ether and the solution was cooled to 0° C. in an ice-bath. 4.0 ml (56 mmole) acetyl chloride were added dropwise under nitrogen. After the first drops, a white salt precipitated out and the temperature increased slightly. After 15 hours at RT, the mixture was decanted and the solid was washed three times with 100 ml ether each time, filtered over an inert gas frit under nitrogen and dried to constant weight under an oil-pump vacuum. 7.7 g benzylidenedimethylammonium chloride (80.9% of theoretical) were obtained in this manner.

2nd stage:

2-(Dimethylaminophenylmethyl)cyclohexanone.

7.1 ml (44 mmole) of 1-(pyrrolidino)-1-cyclohexene were dissolved in 45 ml methylene chloride and the solution was cooled to −70° C. with a dry ice/isopropanol bath under nitrogen. 7.5 g (44 mole) of benzylidenedimethylammonium chloride from stage 1 were added, while stirring, and the mixture was warmed to −30° C. in the course of two to three hours and kept at this temperature for 15 hours. For working up, 60 ml half-concentrated hydrochloric acid were added and the mixture was subsequently stirred for 5 minutes. It was washed with 50 ml ether at RT, 440 ml ammonia solution (25 vol. %) were added to the aqueous phase and the mixture was rapidly extracted three times with 150 ml ether each time. The combined organic extracts were dried over sodium sulfate, filtered and concentrated on a rotary evaporator without heat being supplied (500 to 10 mbar). 10.1 g crude base (99.5% of theory) were obtained in this manner. 9.81 g (42.4 mmole) of the crude base were dissolved in 83 ml 2-butanone, and 0.76 ml (42.2 mmole) water and 5.36 ml (42.4 mmole) chlorotrimethylsilane were added in succession. The mixture was kept at RT for 15 hours and the solid which had precipitated was filtered out with suction, washed with small portions of ether and dried to constant weight in an oil-pump vacuum. 8.92 g of the hydrochloride of 2-(dimethylaminophenylmethyl)cyclo-hexanone (78.6% of theoretical) were obtained in this manner.

3rd stage:

2-(Dimethylaminophenylmethyl)cyclohexanol.

3.0 g (13.0 mmole) of the 2-(dimethylaminophenylmethyl)cyclohexanone prepared according to Example 1 (2nd stage), dissolved in 26 ml toluene, were added dropwise to 26 ml (39 mmole) diisobutylaluminium hydride (1.5 M in toluene) at RT under nitrogen. The mixture was heated under reflux for 15 hours, while stirring. For working up, 13 ml ethanol and 13 ml water were slowly added dropwise and the suspension was stored at 0° C. for several hours, filtered through a glass frit and washed several times with a little toluene. The filtrate was concentrated on a rotary evaporator (500 to 10 mbar) and residues of solvent were removed under a high vacuum (approx. 0.1 mbar). 2.62 g (86.6% of theoretical) 2-(dimethylaminophenylmethyl)-cyclohexanol were obtained.

4th stage:

Dimethyl-{[2-(2-methylbenzyloxy)cyclohexyl] phenylmethyl}-amine hydrochloride.

1.00 g (4.29 mmole) of 2-(dimethylaminophenylmethyl)-cyclohexanol were dissolved in 5.0 ml dimethylsulfoxide, analytical grade, and 577 mg (5.14 mmole) potassium tert-butylate, dissolved in 1.0 ml dimethylsulfoxide, analytical grade, were added under nitrogen. The reaction mixture was heated at 50° C. for 30 minutes, 904 mg (6.43 mmole) 2-methylbenzyl chloride were added dropwise and the mixture was stirred at 50° C. for a further 15 hours. For working up, 10 ml water were added and the mixture was extracted three times with 15 ml ether each time. The combined extracts were washed with 10 ml each of potassium hydroxide solution (2 M) and water and extracted three times with 25 ml hydrochloric acid (5 wt. %) each time. The combined acid extracts were rendered alkaline (pH≧10) with sodium hydroxide solution (32 wt. %) and extracted three times with 25 ml methylene chloride each time. The combined organic extracts were dried over sodium sulfate, filtered and concentrated on a rotary evaporator (500 to 10 mbar). 414 mg of crude base were obtained. The crude base was dissolved in 4 ml 2-butanone, and 11 μl (0.61 mmole) water and 155 μl (1.22 mmole) chlorotrimethylsilane were added in succession. The mixture was stored at RT for 15 hours and the solid which had precipitated was filtered out with suction, washed with small portions of ether and dried to constant weight under an oil-pump vacuum. 221 mg of the hydrochloride of dimethyl-{[2-(2-methylbenzyloxy) cyclohexylphenylmethyl}amine (13.8% of theoretical), which decomposes from 79° C. on heating, were obtained in this manner.

Example 2

[2-(Dimethylaminophenylmethyl)cyclohexyl]-4-trifluoromethylbenzoate hydrochloride.

1st stage:

2-(Dimethylaminophenylmethyl)cyclohexanol.

A total of 28.3 g (747 mmole) sodium borohydride, dissolved in 650 ml methanol, were added in portions to 80.0 g (299 mmole) of the 2-(dimethylaminophenylmethyl) cyclohexanone prepared according to Example 1 (2nd stage), and the mixture was subsequently stirred for one hour. For working up, 680 ml dilute hydrochloric acid (1 N) were added, and the mixture was extracted with 500 ml ether. The aqueous phase was rendered alkaline (pH≧10) with 25 vol. % ammonia solution and extracted three times with 250 ml ether each time. The combined organic extracts were dried over sodium sulfate, filtered and concentrated on a rotary evaporator (500 to 10 mbar). 65.2 g (94% of theoretical) 2-(dimethylaminophenylmethyl)cyclohexanol were obtained.

2nd stage:

[2-(Dimethylaminophenylmethyl)cyclohexyl]4-trifluoromethylbenzoate hydrochloride.

1.34 g (6.43 mmole) of 4-(trifluoromethyl)benzoyl chloride were dissolved in 4 ml methylene chloride, and 870 mg (8.57 mmole) triethylamine were added at −10° C. (methanol/ice cooling bath). 1.0 g (4.29 mmole) 2-(dimethylaminophenylmethyl)cyclohexanol, dissolved in 2 ml methylene chloride, was then added dropwise, and the mixture was subsequently stirred for 15 hours. For working up, 2 ml potassium hydroxide solution (0.5 N) were added and the organic phase was separated, dried over sodium sulfate, filtered and concentrated on a rotary evaporator (500 to 10 mbar). 1.7 g of crude base were obtained. 877 mg of the hydrochloride of [2-(dimethylaminophenyl-methyl) cyclohexyl]4-trifluoromethylbenzoate (34% of theoretical) with a melting point above 230° C. were obtained from the crude base in accordance with Example 1 (4th stage) using chloro-trimethylsilane/water in 2-butanone.

Example 3

[2-(Dimethylaminophenylmethyl)cyclohexyl]4-methoxybenzoate hydrochloride.

1.06 g (6.43 mmole) of 4-methoxybenzoyl chloride were dissolved in 4 ml methylene chloride, and 870 mg (8.57 mmole) triethylamine were added at −10° C. (methanol/ice cooling bath). 1.0 g (4.29 mmole) of the 2-(dimethylaminophenylmethyl)cyclohexanol prepared according to Example 2 (1st stage), dissolved in 2 ml methylene chloride, was then added dropwise, and the mixture was subsequently stirred for 15 hours. For working up, 2 ml potassium hydroxide solution (0.5 N) were added, and the organic phase was separated, dried over sodium sulfate, filtered and concentrated on a rotary evaporator (500 to 10 mbar). 1.78 g of crude base were obtained. 1.00 g of the hydrochloride of [2-(dimethylaminophenylmethyl)-cyclohexyl]4-methoxybenzoate (58% of theoretical) with a melting point above 230° C. was obtained from the crude base in accordance with Example 1 (4th stage) using chlorotrimethylsilane/water in 2-butanone.

Example 4

{[2-(2-Chlorobenzyloxy)cyclohexyl]-(2-chlorophenyl) methyl}-dimethylamine hydrochloride.

1st stage:

2-[(2-Chlorophenyl)dimethylaminomethyl]-cyclohexanone.

17.4 g (213 mmole) of freshly dried dimethylamine hydrochloride were added, while stirring, to 471 mg (469 mmole) sodium iodide solution (1 M in acetonitrile), which was cooled to 0° C. with an ice-bath; 60 ml (427 mmole) triethylamine and 60 ml (469 mmole) chlorotrimethylsilane were added dropwise, and the mixture was subsequently stirred at RT for one hour. While cooling with ice, 24 ml (213 mmole) 2-chlorobenzaldehyde were added, and stirring was continued at RT for a further hour. The mixture was cooled again to 0° C. with an ice-bath; 34 ml (213 mmole) 1-(pyrrolidino)-1-cyclohexene were added, and stirring was continued at RT for two hours. For working up, 300 ml half-concentrated hydrochloric acid were added to the mixture, while cooling with ice, and the mixture was stirred for 10 minutes, washed twice with 300 ml ether each time and rendered alkaline (pH approx. 9) with 770 ml dilute ammonia solution (5 vol. %). The mixture was extracted three times with 300 ml ether each time, and the combined organic extracts were dried over sodium sulfate, filtered and concentrated on a rotary evaporator (500 to 10 mbar) without heat being supplied. 38.3 g 2-[(2-chlorophenyl) dimethylaminomethyl]cyclohexanone (68% of theoretical) were obtained in this manner.

2nd stage:

2-[(2-Chlorophenyl)dimethylaminomethyl]-cyclohexanol hydrochloride.

10.0 g (37.6 mmole) of 2-[(chlorophenyl) dimethylaminomethyl]-cyclohexanone were dissolved in 190 ml methanol, and 2.85 g (75.2 mmole) sodium borohydride were introduced in portions. For working up, 170 ml hydrochloric acid (1 M) were added, while stirring, and the mixture was extracted with 100 ml ether. It was rendered alkaline (pH≧10) with 15 ml ammonia solution (25 vol. %) and extracted three times with 100 ml ether each time. The combined extracts were dried over anhydrous sodium sulfate, filtered and concentrated on a rotary evaporator (500 to 10 mbar). 8.10 g of crude base (80.3% of theoretical) were obtained. 1.74 g of the hydrochloride of 2-[(2-chlorophenyl) dimethyl-aminomethyl]cyclohexanol (78% of theoretical), which decomposes from 131° C., were obtained from 1.98 g (7.39 mmole) of this base in accordance with Example 1 (4th stage) using chlorotrimethylsilane/water in 2-butanone.

3rd stage {[2-(2-Chlorobenzyloxy)cyclohexyl]-(2-chlorophenyl)methyl}-dimethylamine hydrochloride.

902 mg (5.60 mmole) of 2-chlorobenzyl chloride and 1.0 g (3.73 mmole) 2-[(2-chlorophenyl)dimethylaminomethyl]-cyclohexanol were dissolved in 6.0 ml dimethylsulfoxide, analytical grade, 503 mg (4.48 mmole) solid potassium tert-butylate were added, under nitrogen, and the mixture was heated at 100° C. for 15 hours. For working up, 10 ml water were added, and the mixture was extracted three times with 15 ml ether each time. The combined extracts were washed with 10 ml each of potassium hydroxide solution (2 M) and water and extracted three times with 25 ml hydrochloric acid (5 wt. %) each time. The combined acid extracts were rendered alkaline (pH≧11) with sodium hydroxide solution (32 wt. %) and extracted three times with 25 ml methylene chloride each time. The combined organic extracts were dried over sodium sulfate, filtered and concentrated on a rotary evaporator (500 to 10 mbar). 277 mg crude base were obtained. 151 mg {[2-(2-chlorobenzyloxy) cyclohexyl]-(2-chlorophenyl)methyl}-dimethylamine hydrochloride (9.4% of theoretical) with a melting range of 108–100° C. were obtained from this crude base in accordance with Example 1 (4th stage) using chlorotrimethylsilane/water in 2-butanone.

Example 5

{[2-(3-Fluorobenzyloxy)cyclohexyl]-phenylmethyl}dimethylamine hydrochloride.

1.00 g (4.29 mmole) of the 2-(dimethylaminophenylmethyl)cyclohexanol prepared according to Example 1 (3rd stage) were dissolved in 5 ml dimethylsulfoxide, analytical grade, and 503 mg (4.48 mmole) potassium tert-butylate were added at 50° C. The mixture was then heated to 100° C. and 323 μl (2.61 mmole) 3-fluorobenzyl chloride were added. This addition was repeated twice more after in each case two hours, and the reaction mixture was then heated at 100° C. for a further 15 hours. Working up was carried out according to Example 1 (4th stage), as a result of which 166 mg {[2-(3-fluorobenzyloxy)cyclohexyl]phenylmethyl}-dimethylamine hydrochloride (11% of theoretical), which decomposes from 203° C. on heating, were obtained.

Example 6

{[2-(4-Fluorobenzyloxy)cyclohexyl]-phenylmethyl}dimethylamine hydrochloride.

A solution of 1.00 g (4.29 mmole) of the 2-(dimethylaminophenylmethyl)cyclohexanol prepared according to Example 2 (1st stage) in 5 ml dimethylformamide, analytical grade, was added to a suspension of 108 mg (4.48 mmole) sodium hydride in 1 ml dimethylformamide, analytical grade. The reaction mixture was heated to 100° C., and 323 ml (2.61 mmole) 3-fluorobenzyl chloride were added. This addition was repeated twice more after in each case two hours, and the reaction mixture was then heated at 100° C. for a further 15 hours. Working up was carried out according to Example 1 (4th stage), as a result of which 393 mg {[2-(4-fluorobenzyloxy)-cyclohexyl]phenylmethyl}dimethylamine hydrochloride (24% of theoretical), which decomposes from 210° C. on heating, were obtained.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A [3-Amino-3-arylpropan-1-ol] *3-amino-3-arylpropan-1-ol* compound corresponding to formula I

I

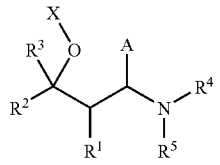

wherein $R^1$ and $R^2$ each independently denote $C_{1-6}$-alkyl, or $R^1$ and $R^2$ together form a $(CH_2)_{2-6}$ ring, which can also be benzo-fused or phenyl-substituted;

$R^3$ denotes H or methyl;

$R^4$ and $R^5$ each independently denote $C_{1-6}$-alkyl, $C_{3-6}$-cycloalkyl, phenyl, benzyl or phenethyl, or $R^4$ and $R^5$ together form a $(CH_2)_{3-6}$ or $CH_2CH_2OCH_2CH_2$ ring;

A denotes a substituted or unsubstituted aryl radical, which optionally contains heteroatoms in the ring system;

X denotes a substituted benzyl group corresponding to formula XI

XI

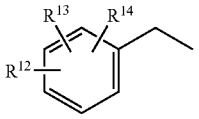

or a substituted benzoyl group corresponding to formula XII

XII

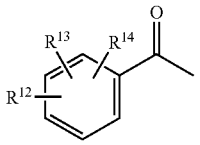

wherein $R^{12}$ to $R^{14}$ each independently denote H, F, Cl, Br, $CHF_2$, $CF_3$, [$OR^{11}$, $SR^{11}$] *$OR^{15}$, $SR^{15}$*, $OCF_3$, $SO_2CH_3$, $SO_2CF_3$, $C_{1-6}$-alkyl, phenyl, CN, [$COOR^{11}$] *$COOR^{15}$* or $NO_2$, where

[$R^{11}$] *$R^{15}$* denotes H, $C_{1-6}$-alkyl, phenyl, benzyl, or phenethyl;

and diastereomers or enantiomers thereof, or a salt thereof with a physiologically acceptable acid,

*with the proviso that if R1 and $R^2$ together form a $(CH_2)_4$ ring, $R^3$ is H, A is a substituted phenyl group corresponding to formula XIII*

XIII

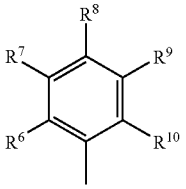

*in which one of $R^6$ to $R^{10}$ is OH and the remainder of $R^6$ to $R^{10}$ are H, and X is a benzyl group corresponding to formula XI in which $R^{12}$ to $R^{14}$ are all H, then $R^4$ and $R^5$ are not both $C_{1-2}$-alkyl.*

2. A compound according to claim 1, wherein $R_1$ and $R^2$ together form a $(CH_2)_6$ ring, which can be benzo-fused or phenyl-substituted.

3. A compound according to claim 1, wherein [$R_1$] *$R^1$* and $R^2$ together form a $(CH_2)_4$ ring, which can be benzo-fused or phenyl-substituted.

4. A compound according to claim 1, wherein $R^3$ represents hydrogen.

5. A compound according to claim 1, wherein A is a substituted phenyl group corresponding to formula XIII

XIII

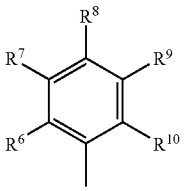

wherein $R^6$ to $R^{10}$ each independently denote H, F, Cl, Br, I, $CF_3$, OH, $OR^{11}$, $OCF_3$, $SR^{11}$, $SO_2CH_3$, $SO_2CF_3$, $C_{1-6}$-alkyl, phenyl, CN, $COOR^{11}$ or $NO_2$, or $R^6$ and $R^7$ or $R^7$ and $R^8$ together form an $OCH_2O$ or $OCH_2CH_2O$ ring, and $R^{11}$ denotes $C_{1-6}$-alkyl, phenyl, benzyl, or phenethyl, or a substituted or unsubstituted thiophene radical or furan radical.

6. A compound according to claim 1, wherein $R^1$ and $R^2$ together form a $(CH_2)_{2-6}$ ring, which can be benzo-fused or phenyl-substituted, and $R^3$ denotes hydrogen.

7. A compound according to claim 5, wherein $R^1$ and $R^2$ together form a $(CH_2)_4$-ring, which can be benzo-fused or phenyl-substituted, and $R^3$ represents hydrogen.

8. A compound according to claim 5, wherein $R^1$ and $R^2$ together form a $(CH_2)_4$-ring, and $R^3$ represents hydrogen.

9. A compound according to claim 1, [characterized in] *wherein* $R^1$ and $R^2$ together form a $(CH_2)_4$ ring, A represents a substituted or unsubstituted thiophene radical, and $R^3$ represents hydrogen.

10. A [compounds] *compound* according to claim 1, wherein $R^1$ and $R^2$ together form a $(CH_2)_4$ ring, A represents a substituted or unsubstituted furan radical, and $R^3$ represents hydrogen.

11. A [compounds] *compound* according to claim 1, wherein X represents a substituted benzyl group of formula XI.

12. A [compounds] *compound* according to claim 1, wherein said compound is selected from the group consisting of:

dimethyl-{[2-(2-methylbenzyloxy)cyclohexyl]phenylmethyl}-amine and the corresponding hydrochloride;

[2-(dimethylaminophenylmethyl)cyclohexyl]4-trifluoromethylbenzoate and the corresponding hydrochloride;

[2-(dimethylaminophenylmethyl)cyclohexyl]4-methoxybenzoate and the corresponding hydrochloride;

{[2-(2-chlorobenzyloxy)cyclohexyl]-(2-chlorophenyl)-methyl}dimethylamine and the corresponding hydrochloride;

{[2-(3-fluorobenzyloxy)cyclohexyl]phenylmethyl}-dimethylamine and the corresponding hydrochloride, and {[2-(4-fluorobenzyloxy)cyclohexyl]phenylmethyl}-dimethylamine and the corresponding hydrochloride.

13. A pharmaceutical composition comprising at least one compound according to claim 1, and a pharmaceutical carrier or adjuvant.

14. A pharmaceutical composition comprising a mixture of enantiomers of a compound according to claim 1, wherein said enantiomers are present in unequal molar amounts.

15. A pharmaceutical composition according to claim 14, wherein one enantiomer comprises between 5 and 45 wt. % of the enantiomer mixture and the other enantiomer comprises between 55 and 95 wt. % of the enantiomer mixture.

16. A process for preparing a [compound 3-Amino-3-arylpropan-1-ol] *3-amino-3-arylpropan-1-ol* compound corresponding to formula I

I

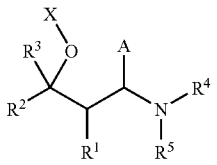

wherein $R^1$ and $R^2$ each independently [denote] *denotes* $C_{1-6}$-alkyl, or $R^1$ and $R^2$ together form a $(CH_2)_{2-6}$ ring, which can also be benzo-fused or phenyl-substituted;

$R^3$ denotes H or methyl;

$R^4$ and $R^5$ each independently [denote] *denotes* $C_{1-6}$-alkyl, $C_{3-6}$-cycloalkyl, phenyl, benzyl or phenethyl, or $R^4$ and $R^5$ together form a $(CH_2)_{3-6}$ ring or $CH_2CH_2OCH_2CH_2$ ring;

A denotes a substituted or unsubstituted aryl radical, which optionally contains heteroatoms in the ring system;

X denotes a substituted benzyl group corresponding to formula XI

XI

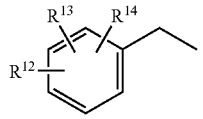

or a substituted benzoyl group corresponding to formula XII

XII

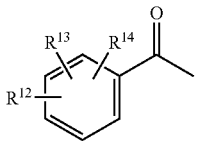

wherein $R^{12}$ to $R^{14}$ each independently [denote] *denotes* H, F, Cl, Br, $CHF_2$, $CF_3$, [$OR^{11}$, $SR^{11}$] $OR^{15}$, $SR^{15}$, $OCF_3$, $SO_2CH_3$, $SO_2CF_3$, $C_{1-6}$-alkyl, phenyl, CN, [$COOR^{11}$] $COOR^{15}$ or $NO_2$, where

[$R^{11}$] $R^{15}$ denotes H, $C_{1-6}$-alkyl, phenyl, benzyl, or phenethyl;

said process comprising reacting a Mannich base corresponding to formula II

II

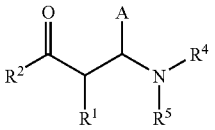

wherein $R^1$ to $R^5$ and A have the meanings given above, with a Grignard compound of formula $(H_3C)Y$, wherein Y denotes MgCl, MgBr, or MgI, or MeLi, or with a reducing agent, to give *rise to* an alcohol corresponding to formula Id Id

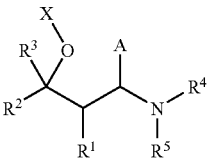

wherein $R^1$ to $R^5$ and A have the meanings given above; and then reacting said alcohol of formula Id with HalX, wherein Hal is a halogen selected from the group consisting of F, Cl, Br, and I, and X has the meaning given above in the presence of an inorganic or organic base at a temperature in the range from 0° to 150° C.; or then condensing said alcohol of formula Id with XOH at a temperature in the range from 0° to 150° C.;

to obtain said compound of formula I.

17. A method according to claim 16, wherein said reducing agent is selected from the group consisting of sodium borohydride, sodium cyanoborohydride, lithium aluminium hydride, diisobutylaluminium hydride, and complex analogues thereof.

18. A method of alleviating pain in a mammal comprising administering to said mammal an effective pain alleviating amount of a compound according to claim 1.

19. A method according to claim 18, wherein said pain is neuropathic pain.

20. A method according to claim 18, wherein said pain is chronic pain.

21. A method of local anaesthesia comprising administering an effective local anaesthesia inducing amount of a compound according to claim 1.

22. A method of treating arrhythmia in a mammal comprising administering to said mammal an effective antiarrhythmic amount of a compound according to claim 1.

23. A method of antiemetic treatment comprising administering an effective antiemetic amount of a compound according to claim 1.

24. A method of nootropic (neurotropic) treatment comprising administering an effective nootropic (neurotropic) amount of a compound according to claim 1.

25. A method of treating cardiovascular disease in a mammal comprising administering to said mammal an effective cardiovascular disease alleviating amount of a compound according to claim 1.

26. A method of treating urinary incontinence in a mammal comprising administering to said mammal an effective urinary incontinence alleviating amount of a compound according to claim 1.

27. A method of treating diarrhea in a mammal comprising administering to said mammal an effective diarrhea inhibiting amount of a compound according to claim 1.

28. A method of treating pruritus comprising administering an effective pruritus alleviating amount of a compound according to claim 1.

29. A method of treating alcohol dependency in a mammal comprising administering to said mammal an effective alcohol dependency alleviating amount of a compound according to claim 1.

30. A method of treating drug dependency in a mammal comprising administering to said mammal an effective drug dependency alleviating amount of a compound according to claim 1.

31. A method of treating medicament dependency in a mammal comprising administering to said mammal an effective medicament dependency alleviating amount of a compound according to claim 1.

32. A method of treating inflammation comprising administering an effective inflammation inhibiting amount of a compound according to claim 1.

* * * * *